US006624125B2

(12) United States Patent
Trage et al.

(10) Patent No.: US 6,624,125 B2
(45) Date of Patent: Sep. 23, 2003

(54) CARE AGENTS

(75) Inventors: Norbert Trage, Gronau (DE); Ralf Bertram, Holzminden (DE); Steffen Sonnenberg, Holzminden (DE); Jürgen Meyknecht, Paris (FR)

(73) Assignee: Haarmann & Reimer GbmH (DE)

( * ) Notice: Subject to any disclaimer, the term of this patent is extended or adjusted under 35 U.S.C. 154(b) by 150 days.

(21) Appl. No.: 09/947,256

(22) Filed: Sep. 5, 2001

(65) Prior Publication Data
US 2002/0111280 A1 Aug. 15, 2002

(30) Foreign Application Priority Data

Sep. 8, 2000 (DE) .......................... 100 44 382

(51) Int. Cl.$^7$ .............. C11D 3/37; C11D 3/50
(52) U.S. Cl. .............. 510/101; 510/438; 510/475
(58) Field of Search ................. 510/101, 475, 510/438

(56) References Cited

U.S. PATENT DOCUMENTS

| 3,971,852 A | * | 7/1976 | Brenner et al. .............. 426/103 |
| 4,331,440 A | * | 5/1982 | Racciato ........................ 8/495 |
| 4,563,187 A | | 1/1986 | Mesmer et al. ................. 8/137 |
| 4,908,233 A | * | 3/1990 | Takizawa et al. ...... 427/213.35 |
| 5,686,405 A | | 11/1997 | Lebreton et al. ............... 512/2 |
| 6,024,943 A | | 2/2000 | Ness et al. .................... 424/59 |
| 6,436,461 B1 | | 8/2002 | Bouwmeesters et al. .... 426/575 |

FOREIGN PATENT DOCUMENTS

| EP | 0 334 490 A2 | 9/1989 |
| EP | 0 539 025 A2 | 4/1993 |
| GB | 1 367 622 | 9/1974 |
| WO | 98/12291 | 3/1998 |

* cited by examiner

Primary Examiner—John Hardee
(74) Attorney, Agent, or Firm—Pendorf & Cutliff

(57) ABSTRACT

Care agents based on matrix particles having a perfume component and washing-active surfactant components can be used in body-cleansing compositions and household cleaners.

23 Claims, No Drawings

CARE AGENTS

FIELD OF THE INVENTION

The invention relates to care agents, which comprise matrix particles having a perfume component and a washing-active surfactant component, wherein the matrix particles preferably consist of a gelatinous polysaccharide. The care agents can be used, for example, in body-cleansing compositions and household cleaners.

BACKGROUND OF THE INVENTION

The encapsulation of products in various technical fields (e.g. medicaments, dyes, foods etc.) is known in order to protect products from undesired influences prior to use, and to use them in a targeted manner.

In the field of care agents, it is known to encapsulate surfactant components and optionally also perfume components as coacervates. Coacervates contain a shell (e.g. made of gelatin, cellulose, gum arabic, polyvinyl alcohol and others, or combinations thereof) and a filling material.

Release of the filling material from the coacervate is only possible by targeted mechanical or physical destruction of the shell. Easy release of the filling material associated with the use is desirable.

As a result of the precipitation processes, loading of the coacervate capsules with relatively large solid or water-soluble constituents is not possible. However, for many application forms, e.g. the uptake of colored particles, this is desired.

SUMMARY OF THE INVENTION

An object of the present invention was to protect care agents, in particular, for body-cleansing and technical use, from undesired impairment prior to use, to be largely unlimited in the choice of ingredients, and to permit easy release of the ingredients upon use.

We have found care agents, which comprise matrix particles having a perfume component and a washing-active surfactant component.

DETAILED DESCRIPTION OF THE INVENTION

The care agent according to the present invention requires the action of only a small force to release the perfume component and optionally, further ingredients. A further unexpected advantage of the matrix particles according to the present invention is that, in contrast to coacervates, they can also be loaded with solid or water-soluble constituents. In the case of coacervates, this is not possible because of the filling process.

Matrix particles for the care agents according to the present invention are known per se (WO 98/15192, Gellan Gum, A Multi-functional Polysaccharide for Gelling and Texturising, Monsanto company brochure from 1992, Technical Bulletin "The Preparation of Kelcogel® Gellan Gum Products" company brochure from The Nutra Sweet Kelco Company RC-137).

The matrix particles for the care agents according to the present invention are multifunctional polysaccharides based on starch, guar, carob seed grain, tragacanth units, xanthan gum, gum arabic, carboxymethylcellulose, alginates, methylcellulose and karaya gum. Particular preference is given to polysaccharides made from glucose, glucuronic acid and rhamnose. Preference is given here to a building block ratio of 2:1:1.

More preferred matrix particles for the care agents according to the present invention contain gellan gum. Gellan gum is a water-soluble polysaccharide obtained by aerobic fermentation from *Pseudomonas eludea*. The microorganisms are supplied by a nutrient medium with a carbon source, phosphates, organic and inorganic nitrogen compounds and trace elements. Prerequisites for growth conditions are sterile working procedures, the introduction of oxygen, agitation, and temperature and pH control. The fermentation mixture is then pasteurized in order to kill the living cells. Gellan gum is obtained from the fermentation mixture.

During the addition reaction of salts onto the carboxyl groups, aggregation of the matrix particles takes place, X-ray diffraction analysis showing that the matrix particles have the structure of a laevorotating parallel double helix, which is folded three times.

Matrix particles having a perfume component can be prepared, for example, by dissolving a multifunctional polysaccharide in water at a suitable hydration temperature, adding the perfume component and preparing an emulsion, the emulsion being added dropwise to an aqueous solution of salts.

Polysaccharide and perfume component are generally used in the ratio 1 to 30, preferably 1 to 20.

Salts are preferably calcium chloride, potassium chloride, magnesium chloride and sodium chloride.

The aqueous solution generally comprises 0.001 to 2 parts by weight, preferably 0.01 to 0.5 parts by weight, of salts.

The size of the matrix particles can be controlled by the size of the dropping capillary.

The care agents according to the present invention generally comprise 0.1 to 20 parts by weight, preferably 5 to 15 parts by weight, more preferably 8 to 12 parts by weight, of matrix particles.

The perfume component can contain one or more, preferably 20 to 60, fragrances.

The perfume component is essentially insoluble in water.

Examples of fragrances for the care agents according to the present invention are given, for example, in S. Arctander, Perfume and Flavor Materials, Vol. I and II, Montclair, N. J., 1969, published privately, or K. Bauer, D. Garbe and H. Surburg, Common Fragrance and Flavor Materials, $3^{rd}$. Ed., Wiley-VCH, Weinheim 1997.

Individual examples which may be mentioned are:

Extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; Davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange flower absolute; orange oil; origanum oil; palmarosa oil; patchouli oil; perilla oil; peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulfur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecenenitrile; 2,12-tridecenenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate, isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octatrien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethyl-cyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2, 1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclo-hexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropyl phenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxy-benzaldehyde; 2-methyl-3-(4-methoxyphenyl)propanal; 2-methyl-3-(4-methylenedioxyphenyl)-propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymole; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl) phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The care agents according to the present invention generally comprise 0.1 to 20 parts by weight, preferably 0.5 to 2 parts by weight, more preferably 0.8 to 1.2 parts by weight, of the perfume component.

The care agents according to the present invention further comprise a washing-active surfactant component. The washing-active surfactant component can consist of one or more, preferably 3 to 5, surfactants.

Washing-active surfactants for the care agents according to the present invention are known per se (Andreas Domsch, Die kosmetischen Präparate, Band II [Cosmetic Preparations, Volume II]).

By way of example, mention may be made of the following washing-active surfactants.

Anionic Surfactants

This class of substance includes secondary alkanesulfonates, e.g. Sodium $C_{14-17}$ alkyl Sec Sulfonate, alkyl sulfates e.g. Sodium Lauryl Sulfate, alkyl ether sulfates, lauryl ether sulfates e.g. Sodium Laureth Sulfate, olefinsulfonates, e.g. Sodium Olefin $C_{14-16}$ Sulfonate, alkylamide ether sulfates, e.g. TEA-PEG-3 Cocamide Sulfate, acyl isethionates e.g. Sodium Cocoyl Isethionate, acyl glutamates e.g. Lauroyl Glutamate, alkyl ether carboxylates e.g. Trideceth-7 Carboxylic Acid, methyl taurides e.g. Sodium Lauroyl Taurate, sarcosides, e.g. Ammonium Cocoyl Sarcosinate, sulfosuccinates, e.g. Disodium PEG-4 Cocamido MIPA-Sulfosuccinate, protein fatty acid condensates e.g. Potassium Cocoyl Hydrolyzed Collagen.

Amphoteric Surfactants

This class of substance includes alkylbetaines, e.g. Lauryl Betaine, alkylamidobetaines e.g. Cocamidopropyl Betaine, sulfobetaines e.g. Cocamidopropyl Hydroxysultaine, acetates and diacetates, e.g. Disodium Cocoamphodiacetate, imidazolines, e.g. Amphonyl, propionates. e.g. Sodium Cocoamphopropionate.

Nonionic Surfactants

This class of substance includes ethoxylated castor oil derivatives, e.g. PEG-20 Hydrogenated Castor Oil, polysorbates, e.g. Polysorbate 80, glycerol fatty acid ester ethoxylates, e.g. PEG 20 Glyceryl Isostearate, sugar surfactants, e.g. capryl/caprylyl glucosides, amine oxides, e.g. Cocamine Oxide.

The care agents according to the present invention generally contains 0.1 to 50 parts by weight, preferably 1 to 20 parts by weight, more preferably 5 to 10 parts by weight, of the washing-active surfactant component.

The care agents according to the present invention comprise water as a further component.

Furthermore, the care agents according to the present invention can also contain electrolytes.

Examples of electrolytes for the care agents according to the present invention which may be mentioned are: sodium chloride, ammonium chloride and magnesium chloride.

The care agents according to the present invention can generally comprise 0.1 to 5 parts by weight, preferably 0.3 to 3 parts by weight, particularly preferably 0.5 to 2 parts by weight, of electrolytes.

The care agents according to the present invention can be prepared as follows:

The gellan gum is dissolved in water at about 70° C., then cooled to about 55° C., and the perfume component is added. The solution is homogenized using a high-speed stirrer and cooled to about 45° C. with stirring. The solution is stirred throughout the entire preparation. A dosing pump is used to pump the solution into an ice-cooled aqueous calcium bath with a calcium ion concentration of about 6 mmol.

The washed matrix particles are added to the surfactant formulation.

The care agents prepared by this process contain matrix particles with a spherical diameter of from 3 to 5 mm. The shape of the particles is uniformly round. The particles have an average degree of hardness and can be destroyed without targeted mechanical action, as arises, for example, during the showering or washing operation.

The care agents according to the present invention can be used in the field of body-cleansing and in technical cleaners, e.g. household cleaners.

Surprisingly, the care agents according to the present invention based on matrix particles have a high retention behavior for (surfactant components), perfume oils and other active ingredients.

It is readily possible to also add solid components, for example, color pigments, to the matrix particles.

One advantage of the care agents according to the present invention based on matrix particles is their simple formulation make-up and an uncomplicated preparation process. The uncomplicated arrangement of apparatus can, therefore, be transferred easily to production scale.

The present invention displays the following further unexpected advantages:

Care agents with the matrix particles according to the present invention do not tend toward "bleeding" of the filling material Care agents based on the matrix particles have high odor stability in surfactant systems Care agents based on the matrix particles have high chemical stability and adhesive effect The care agents according to the present invention based on matrix particles permit a targeted use of the surfactant and perfume components and do not have a negative impact on the environment as a result of a high concentration.

The invention is further illustrated but is not intended to be limited by the following examples in which all parts and percentages are by weight unless otherwise specified.

EXAMPLES

1. Shower gel with matrix particles and carbopol for protecting against sedimentation or creaming:

TABLE I

|  | % content |
|---|---|
| Water | 42.9 |
| Carbopol ETD 2020 | 1.0 |
| Propylene glycol | 5.0 |
| Ethanol | 5.0 |
| Triethanolamine | 1.0 |
| TEA lauryl sulfate | 30.0 |
| Preservative | 0.1 |
| Texapon SB 3 KC | 2.0 |
| Lauramide DEA | 2.0 |
| Matrix particles with 10% perfume | 10.0 |

2. Foaming shower preparation:

TABLE 2

|  | % content |
|---|---|
| Water | 67.3 |
| Plantacare PS 10 | 8.7 |
| Texapon ASV | 5.7 |
| Tego Betaine L7 | 5.7 |
| Cetiol HE | 1.0 |
| Preservative | 0.5 |
| Polymer JR 400 | 0.1 |
| Keltrol BT | 1.0 |
| Matrix particles with 10% perfume | 10.0 |

3. Dishwashing detergent

TABLE 3

|  | % content |
|---|---|
| Marlon A360 | 25.0 |
| Marlipal O13/90 | 4.0 |
| Serdolamide PPF 67 | 1.0 |
| Ethanol | 3.0 |
| Urea | 2.0 |
| Keltrol BT | 1.0 |
| Matrix particles with 2% perfume | 10.0 |
| Water, preservative | 54.0 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Care agents comprising matrix particles having a perfume component and a washing-active surfactant component wherein the matrix particles comprise a gelatinous polymer of glucose, glucouronic acid and rhamnose.

2. Care agents according to claim 1, comprising 0.1 to 50 parts by weight of a washing-active surfactant component.

3. Care agents according to claim 2, comprising 1 to 20 parts by weight of a washing-active surfactant component.

4. Care agents according to claim 3, comprising 5 to 10 parts by weight of a washing-active surfactant component.

5. Care agents according to claim 1, comprising 0.1 to 20 parts by weight of matrix particles.

6. Care agents according to claim 5, comprising 5 to 15 parts by weight of matrix particles.

7. Care agents according to claim 6, comprising 8 to 12 parts by weight of matrix particles.

8. Care agents according to claim 1, comprising 60 to 99 parts by weight of water.

9. Care agents according to claim 8, comprising 65 to 95 parts by weight of water.

10. Care agents according to claim 9, comprising 80 to 90 parts by weight of water.

11. Care agents according to claim 1, comprising a perfume component.

12. Care agents according to claim 11, comprising 0.1 to 20 parts by weight of perfume component.

13. Care agents according to claim 12, comprising 0.3 to 5 parts by weight of perfume component.

14. Care agents according to claim 13, comprising 0.5 to 2 parts by weight of perfume component.

15. Care agents according to claim 1, comprising 0.1 to 10 parts by weight of an electrolyte.

16. Care agents according to claim 15, comprising 0.2 to 5 parts by weight of an electrolyte.

17. Care agents according to claim 15, comprising 0.3 to 3 parts by weight of an electrolyte.

18. Care agents according to claim 1, wherein the matrix particles comprise a diameter of from 0.01 to 20 mm.

19. Care agents according to claim 18, wherein the matrix particles comprise a diameter of from 0.1 to 10 mm.

20. Care agents according to claim 1, wherein the matrix particles comprise a gelatinous polymer of glucose, glucuronic acid and rhamnose in the ratio 2:1:1.

21. Care agents according to claim 1, wherein the matrix particles comprise fillers, cosmetic additives, dyes or active ingredients.

22. Body cleansing compositions comprising care agents which comprise matrix particles having a perfume component and a washing-active surfactant component wherein the matrix particles comprise a gelatinous polymer of glucose, glucouronic acid and rhamnose.

23. Housecleaning products comprising care agents which comprise matrix particles having a perfume component and a washing-active surfactant component wherein the matrix particles comprise a gelatinous polymer of glucose, glucouronic acid and rhamnose.

* * * * *